United States Patent [19]

Descamps et al.

[11] 4,374,841
[45] Feb. 22, 1983

[54] PYRIDOXINE DERIVATIVES, AND USE IN THERAPEUTICS

[75] Inventors: Marcel Descamps, Rosieres, Belgium; Marcel Urbain, deceased, late of Waterloo, Belgium; Claire Urbain, legal representative, Waterloo, Belgium; Jacques J. Z. Urbain, legal representative, Lasne, Belgium; Jean P. M. C. Urbain, legal representative; Nadine C. J. Urbain, legal representative, both of Waterloo, Belgium

[73] Assignee: S. A. Labaz N.V., Brussels, Belgium

[21] Appl. No.: 262,449

[22] Filed: May 11, 1981

[30] Foreign Application Priority Data

May 19, 1980 [GB] United Kingdom ................ 8016516

[51] Int. Cl.$^3$ .................... C07D 213/67; A61K 31/44
[52] U.S. Cl. .................................... 424/263; 546/300; 546/115
[58] Field of Search ........................ 546/300; 424/263

[56] References Cited

U.S. PATENT DOCUMENTS 4,065,461 12/1977 Ross-Petersen .................... 546/300
4,115,575 9/1978 Frei et al. ............................ 424/263
4,206,117 6/1980 Von Philipsborn et al. ....... 424/246

FOREIGN PATENT DOCUMENTS 864917 9/1978 Belgium ............................. 424/250
6614 1/1980 European Pat. Off. ............ 546/300

OTHER PUBLICATIONS

USAN and the USP Dictionary of Drug Names, Griffiths et al., p. 298, 1978.
Posselt et al., Chem. Abstracts, vol. 90, (13), 103,837-r, Mar. 26, 1979.

Primary Examiner—Alan L. Rotman
Attorney, Agent, or Firm—Mason, Kolehmainen, Rathburn & Wyss

[57] ABSTRACT

Novel pyridoxine derivatives represented by the general formula:

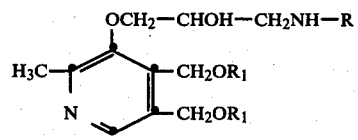

in which:
R represents a radical

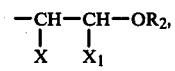

$-CH_2-(CH_2)_n-CH_2-OR_2$ or

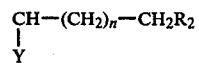

in which n represents 0 or 1, X and $X_1$, which are different, represent hydrogen or methyl, Y represents hydrogen or methyl and $R_2$ represents a phenyl group non-substituted or bearing one or two substituents selected from the group consisting of fluorine, chlorine and bromine and of the radicals methyl, ethyl, n-propyl, isopropyl and methoxy,
$R_1$ represents hydrogen or a radical of formula

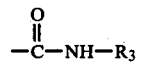

in which $R_3$ represents a straight-chain alkyl radical having from 1 to 4 carbon atoms and pharmaceutically acceptable acid addition salts thereof.

These compounds present α-antiadrenergic properties some of them also presenting β-antiadrenergic, antihypertensive and central depressant effects.

7 Claims, No Drawings

PYRIDOXINE DERIVATIVES, AND USE IN THERAPEUTICS

This invention relates to novel pyridine derivatives and is concerned with novel pyridoxine derivatives and with a method of preparing the said derivatives.

The pyridoxine derivatives with which the present invention is concerned are the compounds represented by the general formula:

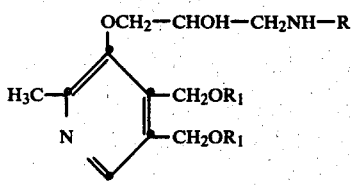

in which:
R represents a radical

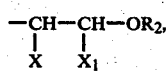

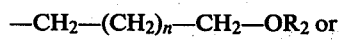

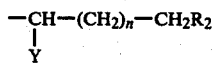

in which n represents 0 or 1, X and $X_1$, which are different, represent hydrogen or methyl, Y represents hydrogen or methyl and $R_2$ represents a phenyl group non-substituted or bearing one or two substitutes selected from the group consisting of fluorine, chlorine and bromine and of the radicals methyl, ethyl, n-propyl, isopropyl and methoxy,
$R_1$ represents hydrogen or a radical of formula

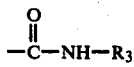

in which $R_3$ represents a straight-chain alkyl radical having from 1 to 4 carbon atoms.

The invention also relates to the pharmaceutically acceptable acid addition salts of the compounds of formula I, for instance those obtained from hydrochloric acid, oxalic acid, fumaric acid, maleic acid and pamoic acid.

One class of compounds falling within the scope of general formula I are those wherein X, $X_1$, Y and n have the same meaning as given therein, $R_2$ represents a phenyl group non-substituted or substituted by one or two methyl radicals, or by a 2-ethyl, 2-n-propyl-, 2-isopropyl-or 2-methoxy-phenyl, a 3,4-dimethyl- or 3,4-dimethoxy-phenyl, a 2-isopropyl-5-methyl-phenyl or a 4-chloro-phenyl group and $R_1$ represents hydrogen or a N-methylcarbamoyl radical as well as the pharmaceutically acceptable acid addition salts thereof.

Examples of compounds falling within the scope of the present invention are listed hereunder:
4,5-Dihydroxymethyl-3-[2-hydroxy-3-(2-methyl-phenoxyethylamino)-propoxy]-2-methyl-pyridine
4,5-Dihydroxymethyl-3-[2-hydroxy-3-(2-phenyl-1-methyl-ethylamino)-propoxy]-2-methyl-pyridine
4,5-Dihydroxymethyl-3-(2-hydroxy-3-phenoxyethylamino-propoxy)-2-methyl-pyridine
4,5-Dihydroxymethyl-3-{2-hydroxy-3-[(3-phenyl-1-methyl-1-propyl)-amino]-propoxy}-2-methyl-pyridine
4,5-Dihydroxymethyl-3-[2-hydroxy-3-(3-methyl-phenoxyethylamino)-propoxy]-2-methyl-pyridine
4,5-Dihydroxymethyl-3-[3-(2-ethyl-phenoxyethylamino)-2-hydroxy-propoxy]-2-methyl-pyridine
4,5-Dihydroxymethyl-3-[3-(2,6-dimethyl-phenoxyethylamino)-2-hydroxy-propoxy]-2-methyl-pyridine
4,5-Dihydroxymethyl-3-[2-hydroxy-3-(3,5-dimethyl-phenoxyethylamino)-propoxy]-2-methyl-pyridine
4,5-Dihydroxymethyl-3-[2-hydroxy-3-(2-methoxy-phenoxyethylamino)-propoxy]-2-methyl-pyridine
4,5-Dihydroxymethyl-3-[2-hydroxy-3-(2-phenoxy-2-methyl-ethylamino)-propoxy]-2-methyl-pyridine
4,5-Dihydroxymethyl-3-[2-hydroxy-3-(1-methyl-2-phenoxy-ethylamino)-propoxy]-2-methyl-pyridine
4,5-Dihydroxymethyl-3-[2-hydroxy-3-(2-isopropyl-5-methyl-phenoxyethylamino)-propoxy]-2-methyl-pyridine
4,5-Dihydroxymethyl-3-[2-hydroxy-3-(4-methyl-phenoxyethylamino)-propoxy]-2-methyl-pyridine
4,5-Dihydroxymethyl-3-[2-hydroxy-3-(2-n-propyl-phenoxyethylamino)-propoxy]-2-methyl-pyridine
4,5-Dihydroxymethyl-3-[2-hydroxy-3-(2-isopropyl-phenoxyethylamino)-propoxy]-2-methyl-pyridine
4,5-Dihydroxymethyl-3-[2-hydroxy-3-(3,4-dimethyl-phenoxypropylamino)-propoxy]-2-methyl-pyridine
4,5-Dihydroxymethyl-3-[2-hydroxy-3-(4-chloro-phenoxyethylamino)-propoxy]-2-methyl-pyridine
4,5-Di-(N-methylcarbamoyloxymethyl)-3-[2-hydroxy-3-(2-methyl-phenoxyethylamino)-propoxy]-2-methyl-pyridine
4,5-Di-(N-methylcarbamoyloxymethyl)-3-(2-hydroxy-3-phenoxyethylamino-propoxy)-2-methyl-pyridine
as well as the pharmaceutically acceptable acid addition salts of these compounds for instance those obtained from hydrochloric acid, oxalic acid, fumaric acid, maleic acid and pamoic acid.

The compounds of formula I hereabove possess in the chain in the 3-position one or more isomeric centres and thus can be produced as optical isomers, position isomers or mixtures of these isomers. The mixture of these isomers can be resolved, if desired, at appropriate stages during their process of preparation by methods known to those skilled in the art to provide the respective individual isomers.

The invention also relates to the individual isomers in question and to racemic mixtures of these isomers.

The pyridoxine derivatives of the invention have been found to possess valuable pharmacological properties capable of rendering them useful in the treatment of arterial hypertension, angina pectoris or in the treatment of circulatory deficiencies in the brain or in the myocardium.

Another object of the invention is concerned with pharmaceutical or veterinary compositions comprising as active ingredient at least one pyridoxine derivative of formula I or a pharmaceutically acceptable acid addition salt of this derivative, in association with a suitable pharmaceutical carrier of excipient.

Another object of the invention is to provide a process for preparing pharmaceutical or veterinary compositions whereby at least one pyridoxine derivative of formula I or a pharmaceutically acceptable acid addition salt thereof, is associated with a suitable pharmaceutical carrier or excipient.

Yet another object of the present invention is to provide a method of treating arterial hypertension, angina pectoris and circulatory deficiencies in the brain or in the myocardium in a subject needing such treatment, which method comprises administering to said subject an effective dose of at least one pyridoxine derivative of formula I or a pharmaceutically acceptable acid addition salt thereof.

The compounds of formula I can be prepared starting from α,α-isopropylidenepyridoxol of formula:

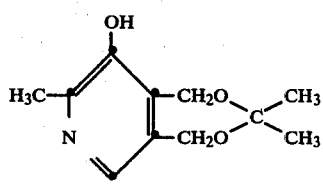

or a salt of this compound, for instance the hydrochloride. The compound of formula II above is a known compound which has been described by W. KORYT-NYK in J. Org. Chem. 1962, 27, 3724.

A. Preparation of the compounds of formula I in which $R_1$ represents hydrogen

The dimethylketal derivative of formula II is first condensed with allyl chloride under reflux and in an appropriate solvent such as a lower alcohol having from 1 to 3 carbon atoms, for instance ethanol or methanol, and in the presence of sodium to give 3-O-allyl-α,α-isopropylidenepyridoxol of formula:

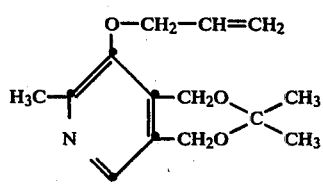

which is further reacted, at room-temperature, with N-bromosuccinimide in the presence of water and in an appropriate solvent, for instance benzene, diethyl ether or diisopropyl ether, to obtain a mixture of two bromhydrines which, after treatment with sodium hydroxide, provides 3-O-(2,3-epoxy-propyl)-α,α-isopropylidenepyridoxol of formula:

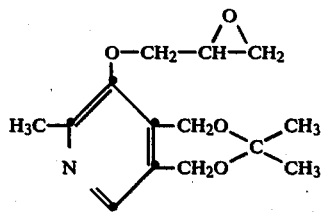

The epoxide of formula IV is then condensed under reflux and in an appropriate solvent such as a lower alcohol having from 1 to 3 carbon atoms, for instance methanol, with a primary amine of general formula:

$$H_2H-R \qquad V$$

in which R has the same meaning as given above.

The intermediate ketal so obtained is subsequently hydrolysed in a strong acid medium, for instance hydrochloric acid, and at a temperature between 25° and 80° C., to obtain the required compounds in free base form.

B. Preparation of the compounds of formula I in which $R_1$ is different from hydrogen The ketal function of the compound of formula III is hydrolysed by means of, for example, hydrochloric acid and the two free hydroxymethyl functions so obtained are then condensed with an appropriate isocyanate of general formula:

$$R_3-N=C=O \qquad VI$$

in which $R_3$ has the same meaning as given above, to provide the compounds of general formula:

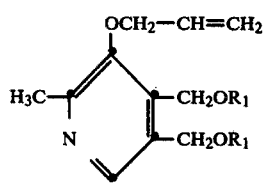

in which $R_1$ represents a

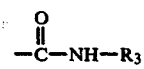

radical as defined above. The compounds of general formula VII are then converted to bromhydrines of general formula:

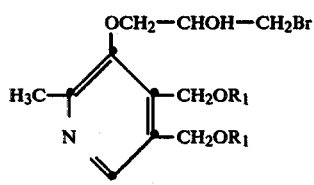

in which $R_1$ represents a

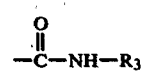

radical as defined above, through the action of N-bromosuccinimide in the presence of water and in a mixture of appropriate solvents, such as an ethyl ether/methylene chloride mixture, to obtain the desired bromhydrines which are then condensed under reflux and in a solvent such as an alcohol from 1 to 3 carbon atoms for instance methanol with an appropriate primary amine of general formula V above, to provide the required compounds of formula I in free base form.

In accordance with another procedure, the compounds of general formula I in which $R_1$ is different from hydrogen can also be obtained by reacting an appropriate alkali metal hydroxide, for example sodium hydroxide, with a bromhydrine of general formula VIII to provide an epoxide of general formula:

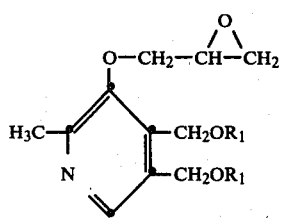

in which $R_1$ represents a

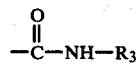

radical as defined above and subsequently condensing this epoxide with an appropriate primary amine of general formula V to obtain the desired compounds in free base form. The pharmaceutically acceptable acid addition salts of the invention, can be obtained, through a classical procedure, by reacting the corresponding pyridoxine derivative of formula I with an appropriate inorganic acid such as, for example, hydrochloric acid or an organic acid such as, for example, oxalic acid, fumaric acid, maleic acid or pamoic acid. Pyridine derivatives are described in U.S. Pat. No. 4,115,575 and a blocking action of adrenergic β-receptors is attributed to them. Likewise, pyridine derivatives are disclosed in Belgian Pat. No. 864,917 as possessing antiarrhythmic and/or local anaesthetic properties.

An enormous number of final products are included within the scope of these patents which cover several pyridoxine derivatives of the present invention through the combination of the various substituents on the pyridine ring which are cited therein.

However, no derivatives having the typical structure of pyridoxine and, in consequence, no derivative of the present invention is specifically cited or described in these references.

Amongst the pyridine derivatives of the aforesaid prior art specific mention is made of derivatives containing a 2-hydroxy-3-N-substituted-amino-propoxy radical. Numerous values are attributed to the substituent on the nitrogen atom of this radical and it is surprising to observe that only alkyl radicals are exemplified namely the t-butyl radical and, in the vast majority of cases, the isopropyl radical.

In the course of the development of the present invention, trials were undertaken using pyridoxine derivatives having, in the 3-position, a 2-hydroxy-3-amino-propoxy radical substituted on the nitrogen atom by one alkyl radical i.e. a n-propyl, isopropyl, 1-methyl-propyl, isobutyl or t-butyl radical or again by a phenoxyalkyl radical i.e. a (2-methoxy-phenoxy)-ethyl or (2-methyl-phenoxy)-ethyl radical.

The purpose of such trials was to verify the pharmacological properties attributed to the compounds described in the above-cited patents. However, the N-alkyl derivatives in question did not show the predicted β-blocking properties or even any antiadrenergic properties of the α- or β-type.

With respect to the phenoxyethyl derivatives, no antiarrhythmic or local anaesthetic properties were observed to any significant degree.

It has now been surprisingly discovered that pyridine derivatives not described in the two above-cited patents and formed from a 4,5-dihydroxymethyl-2-methyl-3-pyridinyl moiety, which is not described in either of the said references, and furthermore having a 2-hydroxy-3-N-substituted-amino-propoxy radical which is also not exemplified in the patents in question, present pharmacological properties quite impossible to predict from the teaching of the prior art.

Thus, it has been found that the replacement of the substituents most frequently exemplified in the prior art i.e. the N-isopropyl or N-t-butyl radicals, by a N-phenoxyalkyl or N-phenylalkyl radical of which the phenyl moiety may be substituted or not, provides pyridoxine derivatives having, as a common feature, powerful antiadrenergic properties with respect to the α-receptors, most of these compounds presenting, in addition, valuable antiadrenergic properties with respect to the β-receptors as well.

Furthermore, some compounds of the invention have been found to present a marked hypotensive effect in the anaesthetized animal with normal blood-pressure and an antihypertensive effect in the conscious animal presenting high blood-pressure.

This effect is probably due to an α-antiadrenergic action which provokes a decrease in the peripheral resistances and probably in part to a reserpine-like effect as well.

Stimulation of the adrenergic receptors by the endogenous catecholamines causes an increase in the work done by the heart and a still greater increase in the cardiac consumption of energy. It is thus recognized that a compound possessing antiadrenergic properties can exert an antianginal action by protecting the myocardium against the hypermetabolizing effect of the catecholamines.

The compounds of the invention which are endowed with α- and β-antiadrenergic activity will, therefore, be indicated in the treatment of angina pectoris also. They will be particularly valuable in this indication because they reduce the work of the myocardium since they cause a decrease in arterial pressure and consequently lower resistance to cardiac ejection.

It is a well-known fact that compounds presenting an α-antiadrenergic action, such as the semi-synthetic ergot of rye derivatives, for example nicergoline, are valuable in the treatment of a certain numberr of cerebral deficiencies of vascular origin, particularly cerebral circulatory insufficiency and migraine.

This effect is particularly valuable in the case of the compounds of the invention since it is linked to a weak central depressant effect which should be accompanied by a decrease on the cerebral metabolism.

For the treatment of cerebral insufficiency, the most valuable compounds of the invention are those which exert the most powerful antiadrenergic effects together with the least potent hypotensive action.

Finally, it has been found quite surprisingly that the compounds of the present invention have a very low degree of toxicity, whether by intravenous or oral route. This imparts to the compounds of the invention a very favourable toxico-pharmacological index which is far superior notably to that of therapeutic compounds presently used in the same indications.

Amongst the compounds of the invention which have shown the most valuable spectrum of pharmacological activity, the following may be cited:

4,5-Dihydroxymethyl-3-[2-hydroxy-3-(2-methyl-phenoxyethylamino)-propoxy]-2-methyl-pyridine and 4,5-Dihydroxymethyl-3-[2-hydroxy-3-(2-methoxy-phenoxyethylamino)-propoxy]-2-methyl-pyridine, these compounds being in the form of the free base or of a pharmaceutically acceptable acid addition salt such as, for example, the oxalate, fumarate or dihydrochloride.

Pharmacological tests carried out with 4,5-dihydroxymethyl-3-[2-hydroxy-3-(2-methyl-phenoxyethylamino)-propoxy]-2-methyl-pyridine in the form of its sesquioxalate (referred to as Compound A hereunder) have shown that this compound possesses α-antiadrenergic properties at a dose as low as 2 mg/kg and an antihypertensive effect from 0.1 to 0.2 mg/kg, both actions being determined by intravenous route in the dog.

Similarly, 4,5-dihydroxymethyl-3-[2-hydroxy-3-(2-methoxy-phenoxyethylamino)-propoxy]-2-methyl-pyridine in the form of its dihydrochloride (referred to as Compound U hereunder) showed prolonged α-antiadrenergic activity at a dose as low as 0.5 mg/kg by intravenous route in the dog. The results of pharmacological tests carried out with the compounds of the invention in order to determine their cardiovascular and central depressant effects are given hereunder.

A. Antiadrenergic properties

The purpose of this test was to determine the capacity of the compounds under study to reduce epinephrine-increased blood-pressure (anti-α effect) and epinephrine-accelerated heart-rate (anti-β effect) in the dog previously anaesthetized with pentobarbital (30 mg/kg) and atropinized (1 mg/kg).

Anti-α effect

For each dog, the dose of epinephrine was first determined which provoked a reproducible increase in arterial pressure of about 100 mm.Hg (between 5 and 10 µg/kg).

After that, the dose of epinephrine so determined was administered followed by a dose, by intravenous route, of the compound to be studied. The percentage of reduction of hypertension produced by the compound under study in comparison with the hypertension previously obtained (about 100 mm.Hg) was then registered.

Anti-β effect

During the same test as that described above, the epinephrine provoked a reproducible increase in the heart-rate of about 70 beats/min. The percentage of reduction of the epinephrine-induced acceleration of heart-rate obtained by means of the compounds under study in comparison with the tachycardia previously measured (about 70 beats) was then registered.

In both cases, the results were expressed as follows:
+ for a <50%-reduction of the increase in pressure or cardiac frequency
++ for a ≧50-reduction of the increase in pressure or cardiac frequency
+++ for the almost complete supression of the increase in pressure or cardiac frequency.

The following results were registered with compounds of formula I used in the form of a salt with oxalic acid.

| R | $R_1$ | Dose (mg/kg) | Anti-α effect | Anti-β effect | Compound |
|---|---|---|---|---|---|
| —(CH₂)₂—O—(2-CH₃-phenyl) | H | 10 | +++ | + | A |
| —(CH₂)₂—O—(2-OCH₃-phenyl) | H | 3.5 | +++ | +++ | B |
| —(CH₂)₂—O—(2,6-diCH₃-phenyl) | H | 10 | +++ | + | C |
| —CH₂—CH(CH₃)—O—phenyl | H | 10 | +++ | ++ | D |
| —CH(CH₃)—CH₂—O—phenyl | H | 7.5 | +++ | + | E |
| —CH(CH₃)—CH₂—phenyl | H | 10 | +++ | ++ | F |
| —(CH₂)₂—O—phenyl | H | 2 | +++ | + | G |

-continued

| R | R₁ | Dose (mg/kg) | Anti-α effect | Anti-β effect | Compound |
|---|---|---|---|---|---|
| -CH(CH₃)-CH₂-CH₂-C₆H₅ | H | 10 | ++ | ++ | H |
| -(CH₂)₂-O-C₆H₃(CH₃)- | H | 10 | ++ | + | I |
| -(CH₂)₂-O-C₆H₃(C₂H₅)- | H | 10 | +++ | + | J |
| -(CH₂)₂-O-C₆H₂(CH₃)(CH₃)- | H | 10 | ++ | ++ | K |
| -(CH₂)₂-O-C₆H₂(CH₃)(CH(CH₃)₂)- | H | 10 | +++ | ++ | L |
| -(CH₂)₂-O-C₆H₄-CH₃ | H | 10 | ++ | 0 | M |
| -(CH₂)₂-O-C₆H₃(n-C₃H₇)- | H | 7 | +++ | ++ | N |
| -(CH₂)₂-O-C₆H₃(CH(CH₃)₂)- | H | 2 | +++ | ++ | P |
| -(CH₂)₂-O-C₆H₃(CH₃)- | CONHCH₃ | 10 | +++ | 0 | Q |
| -(CH₂)₂-O-C₆H₅ | CONHCH₃ | 10 | ++ | 0 | R |
| -(CH₂)₂-O-C₅H₃(CH(CH₃)₂)- (furan) | H | 10 | +++ | ++ | S* |
| -(CH₂)₃-O-C₆H₃(CH₃)(CH₃)- | H | 10 | ++ | ++ | T |
| -(CH₂)₂-O-C₆H₃(OCH₃)- | H | 10 | +++ | ++ | U** |
| -(CH₂)₂-O-C₆H₃-Cl | H | 10 | ++ | + | W |

*used in base form
**used in dihydrochloride form

B. Antihypertensive properties (a) Hypotension in the anaesthetized dog

The hypotensive effect was determined for at least one hour after the intravenous injection of a dose of the compound under study in the dog previously anaesthetized with pentobarbital (30 mg/kg) and atropinized (1 mg/kg).

Arterial pression was registered on a femoral artery.
The results were expressed as follows:
+ + for a lasting reduction of about 30% in arterial pressure
+ for a short-lived reduction of about 20% in arterial pressure.

Trails were undertaken with Compounds A to W above as well as with the compound hereunder in its dioxalate form:

| R | $R_1$ | Compound |
|---|---|---|
| —(CH$_2$)$_2$—(phenyl with OCH$_3$, OCH$_3$) | H | X |

The following results were registered:

| Compound | Dose (mg/kg) | Decrease in arterial pressure |
|---|---|---|
| A | 2 | ++ |
| B | 3.5 | + |
| E | 10 | + |
| G | 2 | ++ |
| F | 10 | + |
| X | 10 | + |

(b) Hypotension in the Okamoto rat

In this trial, the rats used belonged to a race specifically bred to produce animals having high blood-pressure. The arterial pressure of these rats was determined (about 180 mm.Hg) at the beginning of the test and a dose of the compound to be studied was then administered.

The decrease in arterial pressure was registered every hour for 6 hours after the administration of the compound in question.

By oral route, the compound of the invention which was found to be the most active in acute treatment was Compound A above. This compound provoked hypotension at a dose as low as 25 mg/kg inducing a maximum decrease of 21 mm.Hg.

In chronic treatment, involving one single administration, Compound A was found to be active at a dose as low as 50 mg/kg.

C. Reserpine-like properties

These properties were demonstrated after the administration to the anaesthetized dog of successive intravenous injections of 1,2 and 4 mg/kg of the compound to be tested and the following parameters were determined.
the increase in cardiac frequency
the increase of (dP/dt) at its maximum, i.e. the increase of the maximum of the derivative of the left ventricular pressure in relation to time.

This derivative thus represented an index of contractility. Trials were undertaken with Compounds A to X above as well as with the compound hereunder in its oxalate form:

| R | $R_1$ | Compound |
|---|---|---|
| —(CH$_2$)$_2$—(phenyl) | H | Z |

The results showed that Compounds A, C, E, J, L, M, P and Z provoked a 10 to 30%-increase in cardiac frequency and in the contractility of the myocardium at a dose of 1 mg/kg.

At higher doses, the effects indicated hereabove are not increased and can even be reversed.

These effects are suppressed in the dog having previously received reserpine. This was demonstrated notably with Compound A.

Therefore, these effects are induced by the liberation of the intragranular reserve of catecholamines as occurs with the reserpine derivatives thus leading to an antihypertensive effect.

D. Central depressant properties

Thirty minutes after the intragastric administration of a dose of the compound to be studied, batches of mice were placed in a container through which a ray of light was projected. By means of a photoelectric cell, a record was made of the number of animals passing through the light ray over a period of 15 minutes. The same test was performed with control animals.

The $AD_{50}$ was then calculated i.e. the dose of the compound under study which provoked a depressant action in 50% of the animals.

The results hereunder were registered:

| Compound | $AD_{50}$ in mg/kg |
|---|---|
| A | 50 |
| I | 33 |
| J | 47 |
| K | 44 |
| L | 40 |
| N | 42 |
| P | 42 |
| Z | 33 |

E. Acute toxicity

Acute toxicity tests were also undertaken in rats and mice with compounds of the invention.

The following results were registered with the compounds hereunder:

| (I) R | $R_1$ |
|---|---|
| —(CH$_2$)$_2$—O—(phenyl with CH$_3$) | H |

(a) In sesquioxalate form:
(1) In mice
  By intragastric route: $LD_{50}$ = 700 mg/kg
  By intraperitoneal route: $LD_{50}$ = 290 mg/kg
  By intravenous route: $LD_{50}$ = 118 mg/kg
(2) In rats
  By intragastric route: $LD_{50}$ = 2200 mg/kg
  By intraperitoneal route: $LD_{50}$ = 320 mg/kg
  By intravenous route: $LD_{50}$ = 170 mg/kg
(b) In fumarate form
(1) In rats
  By intragastric route: $LD_0$ > 2500 mg/kg
  By intravenous route: $LD_{50}$ = 200 mg/kg

| (II) R | $R_1$ |
|---|---|

-continued

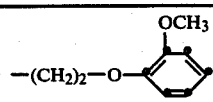

| | |
|---|---|
| (1) In mice | |
| By intragastric route: | LD$_{50}$ > 5000 mg/kg |
| (2) In rats | |
| By intravenous route: | LD$_{50}$ = 245 mg/kg |

It will be appreciated that for therapeutic use the compounds of the invention will normally be administered in the form of a pharmaceutical or veterinary composition, which may be in a dosage unit form appropriate to the desired mode of administration.

Thus the pharmaceutical or veterinary composition may be in a dosage unit form suitable for oral administration for example a coated or uncoated tablet, a hard- or soft-gelatin capsule, a packaged powder or a syrup. The composition may alternatively take the form of a suppository for rectal administration, or of a solution or suspension for parenteral administration.

Irrespective of the form which the composition takes, the pharmaceutical or veterinary composition of the invention will normally be prepared by associating at least one of the compounds of formula I or a pharmaceutically acceptable acid addition salt thereof with an appropriate pharmaceutical carrier or excipient therefor, for example one or more of the following substances: milk sugar, starches, talc, magnesium stearate, polyvinylpyrrolidone, alginic acid, colloidal silica, distilled water, benzyl alcohol or flavoring agents.

The following non-limitative Examples illustrate the preparation of the compounds of the invention together with a therapeutic composition:

EXAMPLE 1

4,5-Dihydroxymethyl-3-[2-hydroxy-3-(2-methyl-phenoxyethylamino)-propoxy]-2-methyl-pyridine and salts thereof (a) 3-O-Allyl-α,α-isopropylidenepyridoxol Into a 1-l flask fitted with a condenser and a stirrer, were poured 400 ml of absolute ethanol to which 9.2 g (0.4 at-g) of sodium were added by fractions. When the reaction was terminated and after cooling, 49.15 g (0.2 mol) of α,α-isopropylidenepyridoxol were added followed by 15.31 g (0.2 mol) of allyl chloride. While stirring, the solution so obtained was refluxed for 4 days. The major part of the ethanol was evaporated off under vacuum and the residue was taken up in water. The medium was extracted with ether and the ethereal extract was washed several times with an aqueous solution of sodium hydroxide (about 2.5 N) and then with water. After drying, the ether was evaporated off and the residue was used as such. In this manner, 30 g of 3-O-allyl-α,α-isopropylidenepyridoxol were obtained.

Yield: 60%

M.P. after recrystallization of the oxalate from ethyl acetate: 97°–98° C.

(b) 3-O-(2,3-Epoxy-propyl)-α,α-isopropylidenepyridoxol

Into a 1-l flask fitted with a stirrer, were poured 200 ml of ethyl ether, 49.8 g (0.2 mol) of 3-O-allyl-α,α-isopropylidenepyridoxol, 36.6 g (0.2 mol) of N-bromosuccinimide and 200 ml of water.

The mixture so obtained was stirred for five days at 20° C.

After neutralization with sodium bicarbonate, the insoluble matter was filtered out and washed with water and ethyl ether. An initial quantity of bromhydrine was thus obtained. A second amount was obtained starting from the ether solution which was washed, dried and evaporated to dryness under vacuum. The residue was taken up in diisopropyl ether or in ethyl ether, thoroughly mixed and then filtered out. The two fractions were collected to provide a mixture of 52 to 55 g which melted at about 130° C. and presented two spots in thin layer chromatography.

This mixture was suspended in 160 ml of ethyl ether and stirred for 4 hours at 20° C. in the presence of 160 ml of a normal aqueous solution of sodium hydroxide. After decantation, washing and drying, the ethyl ether phase was evaporated to dryness under vacuum (Yield: from 90 to 100%). The residue was optionally recrystallized from diisopropyl ether. In this manner, 3-O-(2,3-epoxy-propyl)-α,α-isopropylidenepyridoxol was obtained after crystallization in a yield of about 90%.

M.P.: 76° C.

(c) 4,5-Dihydroxymethyl-3-[2-hydroxy-3-(2-methyl-phenoxyethylamino)-propoxy]-2-methyl-pyridine For 4 hours, a solution was refluxed of 795 g (3 mols) of 3-O-(2,3-epoxy-propyl)-α,α-isopropylidenepyridoxol and 453 g (3 mols) of O-methyl-phenoxyethylamine in 250 ml of methanol. After that, the rection medium was evaporated to dryness under vacuum.

The results was hydrolysed by stirring first for 12 hours at 20° C. in the presence of a solution of 700 ml of hydrochloric acid in 2500 ml of water and then for 30 minutes at 80° C. After cooling, the medium was made alkaline by adding 700 g of potassium carbonate and then extracted first with a 2000 ml/400 ml chloroform/n-butanol mixture and then with 500 ml of chloroform. The organic phases were collected, washed 3 times with water and dried on sodium sulphate. After filtration, 2000 ml of methanol were added.

In this manner, 4,5-dihydroxymethyl-3-[2-hydroxy-3-(2-methyl-phenoxyethylamino)-propoxy]-2-methyl-pyridine was obtained in free base form.

M.P.: about 100° C.

(d) 4,5-Dihydroxymethyl-3-[2-hydroxy-3-(2-methyl-phenoxyethylamino)-propoxy]-2-methyl-pyridine sesquioxalate To the free base obtained above were added 540 g of anhydrous oxalic acid in 1000 ml of methanol. The oxalate which precipitated was filtered out and washed with methanol.

After three crystallizations from methanol, 380 g of 4,5-dihydroxymethyl-3-[2-hydroxy-3-(2-methyl-phenoxyethylamino)-propoxy]-2-methyl-pyridine sesquioxalate were obtained

M.P.: 150°–151° C.

(e) 4,5-Dihydroxymethyl-3-[2-hydroxy-3-(2-methyl-phenoxyethylamino)-propoxy]-2-methyl-pyridine monofumarate Into a flask, 37.6 g (0.1 mol) of the free base obtained in para.c above dissolved in isopropanol were introduced. After that, 23.2 g (0.2 mol) of fumaric acid in isopropanol were added. The medium was refluxed and then concentrated. After this operation ethyl acetate was added and the medium was again concentrated. On cooling, a mass formed which was taken up in ethyl acetate. After filtration, the medium was crystallized from an ethyl acetate/methanol mixture.

In this manner, 4,5-dihydroxymethyl-3-[2-hydroxy-3-(2-methyl-phenoxyethylamino)-propoxy]-2-methyl-pyridine monofumarate was obtained.

M.P.: 119°–120° C. (decomposition)

(f) 4,5-Dihydroxymethyl-3-[2-hydroxy-3-(2-methyl-phenoxyethylamino)-propoxy]-2-methyl-pyridine dihydrochloride Into a flask, 37.6 g (0.1 mol) of the free base obtained in para.c above, dissolved in a methanol/ethyl ether mixture were introduced. After that dry hydrochloric acid was bubbled through and ethyl ether was added. The precipitate so formed was then twice recrystallized from an ethyl acetate/methanol mixture.

In this manner, 4,5-dihydroxymethyl-3-[2-hydroxy-3-(2-methyl-phenoxyethylamino)-propoxy]-2-methyl-pyridine dihydrochloride was obtained. M.P.: 151°–152° C. (decomposition)

(g) 4,5-Dihydroxymethyl-3-[2-hydroxy-3-(2-methyl-phenoxyethylamino)-propoxy]-2-methyl-pyridine dimaleate In a flask, 37.6 g of the free base obtained in para.c above, dissolved in methanol was refluxed in the presence of 23.2 g (0.2 mol) of maleic acid. The mixture was brought to dryness under vacuum and washed twice with dry ethyl ether. After that the medium was crystallized from an acetone/ethyl acetate mixture and then recrystallized from an isopropanol/methanol mixture.

In this manner, 4,5-dihydroxymethyl-3-[2-hydroxy-3-(2-methyl-phenoxyethylamino)-propoxy]-2-methyl-pyridine dimaleate was obtained. M.P.: 113°–116° C.

(h) 4,5-Dihydroxymethyl-3-[2-hydroxy-3-(2-methyl-phenoxyethylamino)-propoxy]-2-methyl-pyridine pamoate In a flask, 37.6 g (0.1 mol) of the free base obtained in para.c above dissolved in methanol was refluxed in the presence of 38.8 g (0.1 mol) of pamoic acid. The mixture was brought to dryness under vacuum and the residue was washed with dry ethyl ether. After that the medium was crystallized from isopropanol and then recrystallized from a methanol/isopropanol mixture.

In this manner, 4,5-dihydroxymethyl-3-[2-hydroxy-3-(2-methyl-phenoxyethylamino)-propoxy]-2-methyl-pyridine pamoate was obtained.

M.P.: 177°–179° C.

Using the same method as that described above, the following compounds were prepared:

| Compound | M.P. °C. |
| --- | --- |
| 4,5-Dihydroxymethyl-3-[2-hydroxy-3-(2-phenyl-1-methyl-ethylamino)-propoxy]-2-methyl-pyridine dioxalate | 98–99 (isopropanol) |
| 4,5-Dihydroxymethyl-3-(2-hydroxy-3-phenoxyethyl-amino-propoxy)-2-methyl-pyridine dioxalate | 110–115 (methanol) |
| 4,5-Dihydroxymethyl-3-{2-hydroxy-3-[3-phenyl-1-methyl-1-propyl)-amino]-propoxy}-2-methyl-pyridine dioxalate | 152–154 (isopropanol/methanol) |
| 4,5-Dihydroxymethyl-3-[2-hydroxy-3-(3-methyl-phenoxyethylamino)-propoxy]-2-methyl-pyridine sesquioxalate | 168–169 (methanol) |
| 4,5-Dihydroxymethyl-3-[3-(2-ethyl-phenoxyethyl-amino)-2-hydroxy-propoxy]-2-methyl-pyridine sesquioxalate | 149–151 (methanol) |
| 4,5-Dihydroxymethyl-3-[3-(2,6-dimethyl-phenoxy-ethylamino)-2-hydroxy-propoxy]-2-methyl pyridine sesquioxalate | 133–135 (methanol) |
| 4,5-Dihydroxymethyl-3-[2-hydroxy-3-(3,5-dimethyl-phenoxyethylamino)-propoxy]-2-methyl-pyridine sesquioxalate | 178–179 (methanol) |
| 4,5-Dihydroxymethyl-3-(2-hydroxy-3-phenylethyl-amino-propoxy)-2-methyl-pyridine oxalate | 160–161 (methanol) |
| 4,5-Dihydroxymethyl-3-[3-(3,4-dimethoxy-phenethylamino)-2-hydroxy-propoxy]-2-methyl-pyridine dioxalate | 116–118 (methanol) |
| 4,5-Dihydroxymethyl-3-[2-hydroxy-3-(2-methoxy-phenoxyethylamino)-propoxy]-2-methyl-pyridine sesquioxalate | 132–133 (methanol) |
| 4,5-Dihydroxymethyl-3-[2-hydroxy-3-(2-phenoxy-2-methyl-ethylamino)-propoxy]-2-methyl-pyridine sesquioxalate | 111–115 (methanol) |
| 4,5-Dihydroxymethyl-3-[2-hydroxy-3-(1-methyl-2-phenoxy-ethylamino)-propoxy]-2-methyl-pyridine oxalate | 180–181 (isopropanol/methanol) |
| 4,5-Dihydroxymethyl-3-[2-hydroxy-3-(2-isopropyl-5-methyl-phenoxyethylamino)-propoxy]-2-methyl-pyridine dioxalate | 164–165 (methanol) |
| 4,5-Dihydroxymethyl-3-[2-hydroxy-3-(4-methyl-phenoxyethylamino)-propoxy]-2-methyl-pyridine sesquioxalate | 133–135 (methanol) |
| 4,5-Dihydroxymethyl-3-[2-hydroxy-3-(2-n-propyl-phenoxyethylamino)-propoxy]-2-methyl-pyridine dioxalate | 143–145 (methanol) |
| 4,5-Dihydroxymethyl-3-[2-hydroxy-3-(2-isopropyl-phenoxyethylamino)-propoxy]-2-methyl-pyridine dioxalate | 165–166 (methanol) |
| 4,5-Dihydroxymethyl-3-[2-hydroxy-3-(3,4-dimethyl-phenoxyethylamino)-propoxy]-2-methyl-pyridine sesquioxalate | 184–185 (methanol) |
| 4,5-Dihydroxymethyl-3-[2-hydroxy-3-(2-isopropyl-phenoxyethylamino)-propoxy]-2-methyl-pyridine | (diisopropyl ether/methanol) |
| 4,5-Dihydroxymethyl-3-[2-hydroxy-3-(3,4-dimethyl-phenoxy-propylamino)-propoxy]-2-methyl-pyridine sesquioxalate | 147–150 (diisopropyl ether/methanol) |
| 4,5-Dihydroxymethyl-3-[2-hydroxy-3-(2-methoxy-phenoxyethylamino)-propoxy]-2-methyl-pyridine dihydrochloride | 107–110 (ethyl acetate/methanol) |
| 4,5-Dihydroxymethyl-3-[2-hydroxy-3-(4-chloro-phenoxyethylamino)-propoxy]-2-methyl-pyridine sesquioxalate | 112–115 (methanol) |

EXAMPLE 2

Preparation of 4,5-di-(N-methylcarbamoyloxymethyl)-3-[2-hydroxy-3-(2-methyl-phenoxyethylamino)-propoxy]-2-methyl-pyridine oxalate (a) 3-Allyloxy-4,5-dihydroxymetyl-2-methyl-pyridine For about 8 hours, 83 g of 3-O-allyl-α,α-isopropylidenepyridoxol were treated, at room-temperature with a solution of 747 ml of water and 83 ml of concentrated hydrochloric acid. The solution so obtained was brought to 50° C. by means of a water-bath and potassium carbonate in excess was added. The solution was extracted with three fractions of chloroform and washed with an aqueous solution of sodium chloride.

This solution was brought to dryness under reduced pressure. The residue was taken up in diisopropyl ether and filtered.

In this manner 64 to 65 g of 3-allyloxy-4,5-dihydroxymethyl-2-methylpyridine were obtained.

Yield: 90–92%

M.P.: ±125° C.

(b) 3-Allyloxy-4,5-di-(N-methylcarbamoyloxymethyl)-2-methyl-pyridine

In a flask, 33.7 g (0.16 mol) of 3-allyloxy-4,5-dihydroxymethyl-2-methyl-pyridine in 150 ml of anhydrous tetrahydrofuran were treated with 80 ml of methyl isocyanate. The mixture was allowed to stand at room-temperature for about 8 hours and then refluxed for 24 hours. The progress of the reaction was controlled by thin layer chromatography (eluent: 45/45/10 mixture of chloroform/hexane/methanol) in the presence of ammonia vapors and the duration of heating was modified as required. The solution was heated to dryness under vacuum using a water bath of 35° to 40° C. The residue was taken up in diisopropyl ether, filtered and washed.

In this manner about 49 g of 3-allyloxy-4,5-di-(N-methylcarbomoyloxymethyl)-2-methyl-pyridine were obtained.

Yield: ≃94%

M.P. ±100°–102° C.

When recrystallized from ethyl acetate, a sample of the desired product melted at 109°–110° C.

(c) 3-(3-Bromo-2-hydroxy-propoxy)-4,5-di-(N-methylcarbamoyloxymethyl)-2-methyl-pyridine In an ethyl ether/methylene chloride mixture were dissolved 43.4 g (0.134 mol) of 3-allyloxy-4,5-di-(N-methylcarbamoyloxymethyl)-2-methylpyridine. To this solution, 130 ml of water were added. While stirring 23.85 g of N-bromosuccinimide were slowly added.

The mixture was then stirred at room-temperature for 3 days. After filtration, the medium was washed with water and ethyl ether to give 40 g of the desired product melting at about 135° C. (yield: 71%).

The organic phase was decanted, washed, dried and brought to dryness under vacuum. The residue was taken up in ethyl acetate mixed with a small fraction of ethyl ether.

A second fraction of 6 g of desired product was thus obtained melting at 126.8° C. (yield: about 10%)

In this manner, 3-(3-bromo-2-hydroxy-propoxy)-4,5-di-(N-methylcarbamoyloxymethyl)-2-methyl-pyridine was obtained.

(d) 4,5-Di-(N-methylcarbamoyloxymethyl)-3-[2-hydroxy-3-(2-methyl-phenoxyethylamino)-propoxy]-2-methyl-pyridine oxalate While stirring a mixture was refluxed for 24 hours of 5 g (0.012 mol) of 3-(3-bromo-2-hydroxy-propoxy)-4,5-di-(N-methyl-carbamoyloxymethyl)-2-methyl-pyridine and 1.81 g (0.012 mol) of O-tolyloxyethylamine in 100 ml of methanol containing 5 g of sodium bicarbonate. This mixture was brought to dryness under reduced pressure and the residue was taken up in a water-/chloroform mixture or in methylene chloride. The organic phase was washed with a little water, dried on sodium sulphate and heated to dryness under vacuum.

The residue was washed with isopropyl ether and dissolved in isopropanol.

After that, a solution of oxalic acid in isopropanol was added and the medium was filtered and crystallized three times from methanol.

In this manner 4,5-di-(N-methycarbamoyloxymethyl)-3-[2-hydroxy-3-(2-methyl-phenoxyethylamino)-propoxy]-2-methyl-pyridine oxalate was obtained.

M.P.: 192°–193° C. (methanol)

Using the same procedure as that described above but starting from the appropriate products the compound hereunder was prepared:

| Compound | M.P. °C. |
| --- | --- |
| 4,5-Di-(N—methylcarbamoyloxymethyl)-3-(2-hydroxy-3-phenoxyethylamino-propoxy)-2-methyl-pyridine oxalate | 172–174 (methanol) |

EXAMPLE 3

Preparation of 4,5-di-(N-methylcarbamoyloxymethyl)-3-[2-hydroxy-3-(2-methyl-phenoxyethylamino)-propoxy]-2-methyl-pyridine.

(a) 4,5-di-(N-methylcarbamoyloxymethyl)-3-(2,3-epoxy-propoxy)-2-methyl-pyridine

Into a flash 33.9 g (0.1 mol) of 3-(3-bromo-2-hydroxy-propoxy)-4,5-di-(N-methylcarbamoyloxymethyl)-2-methyl-pyridine in ethyl ether were introduced. There were then added 8 g (0.2 mol) of sodium hydroxide in water at room-temperature and the medium was maintained at this temperature for 4 hours. After that, the mixture was decanted, washed with water, dried and heated to dryness under vacuum. The residue was then crystallized from diisopropyl ether optionally containing a small amount of methanol.

In this manner, 4,5-di-(N-methylcarbamoyloxymethyl)-3-(2,3-epoxy-propoxy)-2-methyl-pyridine was obtained.

M.P.: ±135° C.

(b) 4,5-di-(N-methylcarbamoyloxymethyl)-3-[2-hydroxy-3-(2-methyl-phenoxyethylamino)-propoxy]-2-methyl-pyridine This compound was prepared from the epoxide previously obtained and O-tolyloxyethylamine in accordance with the process described in Example 2 para. d.

EXAMPLE 4

A unit for oral administration was prepared by introducing 300 mg of 4,5-dihydroxymethyl-3-[2-hydroxy-(2-methyl-phenoxyethylamino)-propoxy]-2-methyl-pyridine sesquioxalate into a soft-gelatin capsule.

We claim:

1. A pyridoxine derivative represented by the general formula:

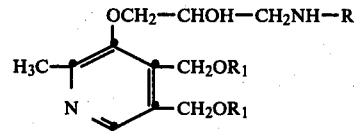

in which: R represents a radical

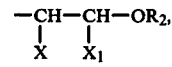

—CH$_2$—(CH$_2$)$_n$—CH$_2$OR$_2$ or

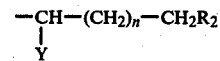

in which n represents 0 or 1, X and X$_1$, which are different, represent hydrogen or methyl, Y represents hydrogen or methyl and R$_2$ represents a phenyl group nonsubstituted or bearing one or two substituents selected from the group consisting of fluorine, chlorine and bromine and of the radicals methyl, ethyl, n-propyl, isopropyl and methoxy, R$_1$ represents hydrogen as well as a pharmaceutically acceptable acid addition salt thereof.

2. A pyridoxine derivative according to claim 1 in which X, X$_1$, Y and n have the same meaning as given therein, $R_2$ represents a phenyl group non-substituted or bearing one of two methyl radicals, a 2-ethyl-, 2-n-propyl-, 2-isopropyl- or 2-methoxy-phenyl, a 3,4-dimethyl- or 3,4-dimethoxy-phenyl, a 2-isopropyl-5-methyl-phenyl or a 4-chloro-phenyl group and $R_1$ represents hydrogen as well as a pharmaceutically acceptable acid addition salt thereof.

3. 4,5-Dihydroxymethyl-3-[2-hydroxy-3-(2-methyl-phenoxyethylamino)-propoxy]-2-methyl-pyridine and pharmaceutically acceptable acid addition salts thereof.

4. 4,5-Dihydroxymethyl-3-[2-hydroxy-3-(2-methoxy-phenoxyethylamino)-propoxy]-2-methyl-pyridine and pharmaceutically acceptable acid addition salts thereof.

5. A pyridoxine derivative according to claims 1, 2, 3 or 4 in the form of a pharmaceutically acceptable acid addition salt obtained from hydrochloric acid, oxalic acid, fumaric acid, maleic acid or pamoic acid.

6. A pharmaceutical or veterinary composition for treating arterial hypertension comprising as active ingredient at least one pyridoxine derivative according to claims 1, 2, 3, 4 or 5 in association with a pharmaceutical carrier or excipient therefor in a daily dosage of about 300 mg per 60 kg of body weight.

7. A method of treating arterial hypertension in a subject needing such treatment which method comprises administering to said subject an effective dose of 0.1 mg/kg to 10 mg/kg of a pyridoxine derivative according to claims 2, 3, 4 or 5.

* * * * *